US009827534B2

(12) United States Patent
Palti

(10) Patent No.: US 9,827,534 B2
(45) Date of Patent: *Nov. 28, 2017

(54) GAS EXCHANGER AND ARTIFICIAL LUNG

(71) Applicant: Yoram Palti, Haifa (IL)

(72) Inventor: Yoram Palti, Haifa (IL)

(*) Notice: Subject to any disclaimer, the term of this patent is extended or adjusted under 35 U.S.C. 154(b) by 121 days.

This patent is subject to a terminal disclaimer.

(21) Appl. No.: 14/837,664

(22) Filed: Aug. 27, 2015

(65) Prior Publication Data
US 2015/0360182 A1 Dec. 17, 2015

Related U.S. Application Data

(63) Continuation-in-part of application No. 14/331,608, filed on Jul. 15, 2014, now Pat. No. 9,138,522.
(Continued)

(51) Int. Cl.
A61M 1/16 (2006.01)
B01D 69/04 (2006.01)
B01D 63/06 (2006.01)
B01D 69/02 (2006.01)
B01D 53/22 (2006.01)

(52) U.S. Cl.
CPC ......... B01D 69/043 (2013.01); A61M 1/1698 (2013.01); B01D 63/06 (2013.01); A61M 2202/0208 (2013.01); A61M 2202/0225 (2013.01); B01D 69/02 (2013.01);
(Continued)

(58) Field of Classification Search
CPC .... A61M 1/14; A61M 1/1678; A61M 1/1698; B01D 69/00–69/148
See application file for complete search history.

(56) References Cited

U.S. PATENT DOCUMENTS 6,350,411 B1  2/2002  Cho et al.
6,667,099 B1  12/2003  Greiner et al.
(Continued)

FOREIGN PATENT DOCUMENTS

DE  10 2007 010 112   2/2007
WO     03/076702      9/2003
(Continued)

OTHER PUBLICATIONS

Yu, Min-Feng et al., Strength and Breaking Mechanism of Multiwalled Carbon Nanotubes Under Tensile Load, Science 287 637-640 (Jan. 28, 2000).
(Continued)

Primary Examiner — Tatyana Zalukaeva
Assistant Examiner — Benjamin Klein
(74) Attorney, Agent, or Firm — Potomac Law Group, PLLC

(57) ABSTRACT

Blood or other fluids can be caused to interact with a gas by providing a plurality of fluid flow channels that are surrounded by nanotubes, each of the channels having an inflow end and an outflow end, wherein each of the channels is wide enough for the blood to flow through, and wherein the nanotubes are spaced close enough to each other to retain the fluid within the channels when the blood is flowing through the channels. The fluid is then passed through the through the channels while a gas is passed through the spaces between the nanotubes outside the fluid flow channels. This permits the gas to interact with the fluid in the channels.

21 Claims, 11 Drawing Sheets

Related U.S. Application Data

(60) Provisional application No. 61/846,888, filed on Jul. 16, 2013.

(52) U.S. Cl.
CPC .... *B01D 2053/223* (2013.01); *B01D 2319/02* (2013.01); *B01D 2325/38* (2013.01)

(56) References Cited

U.S. PATENT DOCUMENTS

| | | | |
|---|---|---|---|
| 9,138,522 B2* | 9/2015 | Palti | ............ A61M 1/1698 |
| 2014/0088725 A1 | 3/2014 | Palti | |

FOREIGN PATENT DOCUMENTS

| | | | | |
|---|---|---|---|---|
| WO | 2011/013075 | | 2/2011 | |
| WO | 2011/091074 | | 7/2011 | |
| WO | WO 2011091074 A3 * | 11/2011 | | .......... A61M 1/1698 |
| WO | 2013/041950 | | 3/2013 | |

OTHER PUBLICATIONS

Mu, Cheng et al., Silicon Nanotube Array/Gold Electrode for Direct Electrochemistry of Cytochrome, J. Phys. Chem. B, 2007, 111, pp. 1491-1495 (2007).

Hou, Chen et al., Reverse Engineering of Oxygen Transport in the Lung: Adaptation to Changing Demands and Resources through Space-Filling Networks. PLoS Comput Bio, vol. 6, Issue 8, p. 1000902. (Aug. 2010).

Li, J. et al. Highly-ordered carbon nanotube arrays for electronics applications, Applied Physics Letters 75, No. 3, pp. 367-369. (Jul. 1999).

Won, Yoonjin et al., Zipping, Entanglement, and the Elastic Modulus of Aligned Single-Walled Carbon Nanotube Films, PNAS vol. 110 No. 51 (Dec. 17, 2013).

Gujarati TP. et al., Abstract of Highly Ordered Vertical Arrays of TiO2/ZnO Hybrid Nanowires: Synthesis and Electrochemical Characterization, J Nanosci Nanotechnol, Aug. 2015; 15(8): 5833-9, 2 pages.

Kashyap, Diwakar et al., Fabrication of Vertically aligned Copper Nanotubes as a Novel Electrode for Enzymatic Biofuel Cells, Electrochimica Acta 167 (2015) 213-218.

Kim, Do Hong et al., Vertically Ordered Hematite Nanotube Array as an Ultrasensitive and Rapid Response Acetone Sensor, ACS Applied Materials & Interfaces (2014), 6, 14779-14784.

Li, Rui et al., Vertically aligned single-crystal zinc sulfide nanotubes with hexagonal cross-sections and optical properties, Materials Letters 154 (2015) 112-115.

Varghese, Oomman K. et al., abstract of Long vertically aligned titania nanotubes on transparent conducting oxide for highly efficient solar cells, Nature Nanotechnology 4, 592-597 (2009).

* cited by examiner

GAS EXCHANGER AND ARTIFICIAL LUNG

CROSS REFERENCE TO RELATED APPLICATIONS

This Application is a continuation-in-part of application Ser. No. 14/331,608, filed Jul. 15, 2014, which claims the benefit of U.S. Provisional Application 61/846,888, filed Jul. 16, 2013. Each of the above-identified applications is incorporated herein by reference in its entirety.

BACKGROUND

The main function of the lung is to exchange gasses between the ambient air and the blood. Within this framework $O_2$ is transferred from the environment to the blood while $CO_2$ is eliminated from the body.

In a normal resting human these processes are associated with an $O_2$ input of about 200-250 $cm^3$/min and an output of about the same amount of $CO_2$. This exchange is made through a surface area of 50-100 $m^2$ of a 0.5-1 μm thick biological membrane separating the alveolar air from the pulmonary blood. This process is associated with the flow of similar volumes of blood and air—about 5 Liter/min. At the given flow rate the blood is in "contact" with the membrane through which diffusion takes place for a time period of ⅓-⅕ sec.

In natural systems such as the lung the gas exchange is achieved by diffusion taking place across a thin biological membrane separating two compartments: the gases in the lung alveoli and the gases contained in the blood of the lung capillaries. The gases in the alveolar compartment are maintained at a composition close to that of ambient air or gas by moving the air or gases in and out of the lungs by respiratory movements. The gas exchange is achieved by diffusion through the surface area of the exchange membrane that is extremely large—about 70 $m^2$. The driving force for diffusion of gases into and out of the blood is maintained by a very large blood flow through the lung capillaries.

Nanotubes ("NT") are inert cylindrical structures having diameters of about 1-100 nm. In the case of carbon NT they are constructed of one or more layers of hexagonal carbon atom mesh. Their length can reach values in the cm range. FIG. 1A depicts a single wall NT made of carbon. At this time, NTs are well-known structures, and ways to make NTs are also well known. FIG. 1B depicts a scanning electron microscope photo of a matrix of parallel aligned carbon nanotubes.

Nanofibers are similar structures made out of carbon, silicon, etc. and are also commercially available. Nanofibers are defined as fibers with diameters less than 100 nanometers (see ref 1). In the textile industry, this definition is often extended to include fibers as large as 1000 nm diameter (see ref 2). Carbon nanofibers are graphitized fibers produced by catalytic synthesis. Inorganic nanofibers (sometimes called ceramic nanofibers) can be prepared from various kinds of inorganic substances, the most frequently mentioned ceramic materials with nanofiber morphology are titanium dioxide (TiO2), silicon dioxide (SiO2), zirconium dioxide (ZrO2), aluminum oxide (Al2O3), lithium titanate (Li4Ti5O12), titanium nitride (TiN) or platinum (Pt).

SUMMARY OF THE INVENTION

One aspect of the invention is directed to a gas exchange unit for processing blood that includes blood cells and plasma. This gas exchange unit includes a substrate having a first side and a second side. A plurality of nanotubes are disposed on the second side of the substrate with spaces between the nanotubes, and the nanotubes are disposed on the substrate in a configuration that leaves a plurality of blood flow channels that are surrounded by the nanotubes, each of the channels having an inflow end and an outflow end. Each of the channels is wide enough for the blood to flow through, and the nanotubes are spaced close enough to each other to retain the plasma within the channels when the blood is flowing through the channels. The substrate has a plurality of perforations that extend between the first side of the substrate and the second side of the substrate, each of the perforations being aligned with a respective one of the channels. This gas exchange unit also includes a blood inlet configured to supply blood to the first side of the substrate, wherein the blood inlet is in fluid communication with the perforations such that blood that arrives via the blood inlet will flow through the perforations and continue on through the channels. It also includes a blood outlet configured to accept blood that arrives from the outflow end of the channels. It also includes a housing configured to house the substrate and the array of nanotubes, the housing having a gas inlet configured to route a gas into the spaces between the nanotubes and a gas outlet configured to route the gas away from the spaces between the nanotubes.

In some embodiments, each of the nanotubes is perpendicular to the substrate and each of the channels is perpendicular to the substrate. In some embodiments, the nanotubes are disposed on the substrate in an array configuration, with a plurality of voids in the array, wherein each of the voids corresponds to a respective channel. In some embodiments, each of the channels has a diameter between 2 and 500 μm. In some embodiments, the nanotubes have a diameter between 5 and 20 nm. In some embodiments, the nanotubes are spaced on centers that are between 1.5 times the diameter of the nanotubes and 5 times the diameter of the nanotubes. In some embodiments, each of the nanotubes is perpendicular to the substrate, each of the channels is perpendicular to the substrate, each of the channels has a diameter between 2 and 500 μm, and the nanotubes have a diameter between 5 and 20 nm. The nanotubes may be spaced on centers that are between 1.5 times the diameter of the nanotubes and 5 times the diameter of the nanotubes. In some embodiments, the nanotubes are disposed on the substrate in an array configuration, with a plurality of voids in the array, wherein each of the voids corresponds to a respective channel.

Another aspect of the invention is directed to a gas exchanger for processing blood that Includes blood cells and plasma. This gas exchanger includes a plurality of gas exchange units. Each of these gas exchange units includes (a) a substrate having a first side and a second side, (b) a plurality of nanotubes disposed on the second side of the substrate with spaces between the nanotubes, wherein the nanotubes are disposed on the substrate in a configuration that leaves a plurality of blood flow channels that are surrounded by the nanotubes. Each of the channels has an inflow end and an outflow end, and each of the channels is wide enough for the blood to flow through. The nanotubes are spaced close enough to each other to retain the plasma within the channels when the blood is flowing through the channels. The substrate has a plurality of perforations that extend between the first side of the substrate and the second side of the substrate, each of the perforations being aligned with a respective one of the channels. Each of these gas exchange units also includes (c) a blood inlet configured to supply blood to the first side of the substrate, wherein the blood inlet is in fluid communication with the perforations such that blood that arrives via the blood inlet will flow through the perforations and continue on through the channels, and (d) a blood outlet configured to accept blood that arrives from the outflow end of the channels. This gas exchanger also includes a housing configured to house the plurality of gas exchange units. The housing has a gas inlet configured to route a gas into the spaces between the nanotubes, and a gas outlet configured to route the gas away from the spaces between the nanotubes. This gas exchanger also includes a blood inflow path configured to route incoming blood to at least one of the gas exchange units, and a blood outflow path configured to route outgoing blood from at least one of the gas exchange units.

In some embodiments, the gas exchange units are interconnected so that the blood flows through the gas exchange units in series. In some embodiments, in each of the gas exchange units, each of the nanotubes is perpendicular to the substrate, each of the channels is perpendicular to the substrate, each of the channels has a diameter between 2 and 500 nm, and the nanotubes have a diameter between 5 and 20 nm. In some embodiments, in each of the gas exchange units, the nanotubes are disposed on the substrate in an array configuration, with a plurality of voids in the array, with each of the voids corresponding to a respective channel. In some embodiments, the gas exchange units are interconnected so that the blood flows through the gas exchange units in parallel.

Another aspect of the invention is directed to a method for processing blood that includes blood cells and plasma. This method includes the steps of providing a plurality of blood flow channels that are surrounded by nanotubes, each of the channels having an inflow end and an outflow end. Each of the channels is wide enough for the blood to flow through, and the nanotubes are spaced close enough to each other to retain the plasma within the channels when the blood is flowing through the channels. This method also includes the steps of passing blood through the through the channels, and passing a gas through the spaces between the nanotubes outside the blood flow channels, wherein the gas interacts with the blood in the channels.

In some embodiments, each of the channels has a diameter between 2 and 500 nm. In some embodiments, the nanotubes have a diameter between 5 and 20 nm. In some embodiments, the nanotubes are spaced on centers that are between 1.5 times the diameter of the nanotubes and 5 times the diameter of the nanotubes.

Another aspect of the invention is directed to an apparatus that includes a substrate having a first side and a second side. A plurality of nanotubes are disposed on the second side of the substrate with spaces between the nanotubes, and the nanotubes are disposed on the substrate in a configuration that leaves a plurality of fluid flow channels that are surrounded by the nanotubes. Each of the channels has an inflow end and an outflow end, each of the channels is wide enough for a fluid to flow through, and the nanotubes are spaced close enough to each other to retain the fluid within the channels when the fluid is flowing through the channels. The substrate has a plurality of perforations that extend between the first side of the substrate and the second side of the substrate, each of the perforations being aligned with a respective one of the channels. This apparatus also includes a fluid inlet configured to supply fluid to the first side of the substrate. The fluid inlet is in fluid communication with the perforations such that fluid that arrives via the fluid inlet will flow through the perforations and continue on through the channels. It also includes a fluid outlet configured to accept fluid that arrives from the outflow end of the channels, and a housing configured to house the substrate and the array of nanotubes. The housing has a gas inlet configured to route a gas into the spaces between the nanotubes and a gas outlet configured to route the gas away from the spaces between the nanotubes.

In some embodiments, each of the nanotubes is perpendicular to the substrate and each of the channels is perpendicular to the substrate. In some embodiments, the nanotubes are disposed on the substrate in an array configuration, with a plurality of voids in the array, wherein each of the voids corresponds to a respective channel.

Another aspect of the invention is directed to an apparatus that includes a plurality of units. Each of the units includes (a) a substrate having a first side and a second side, and (b) a plurality of nanotubes disposed on the second side of the substrate with spaces between the nanotubes. The nanotubes are disposed on the substrate in a configuration that leaves a plurality of fluid flow channels that are surrounded by the nanotubes, each of the channels having an inflow end and an outflow end. Each of the channels is wide enough for a fluid to flow through, and the nanotubes are spaced close enough to each other to retain the fluid within the channels when the fluid is flowing through the channels. The substrate has a plurality of perforations that extend between the first side of the substrate and the second side of the substrate, each of the perforations being aligned with a respective one of the channels. Each of the units also includes (c) a fluid inlet configured to supply fluid to the first side of the substrate, wherein the fluid inlet is in fluid communication with the perforations such that fluid that arrives via the fluid inlet will flow through the perforations and continue on through the channels, and (d) a fluid outlet configured to accept fluid that arrives from the outflow end of the channels. The apparatus also includes a housing configured to house the plurality of units, the housing having a gas inlet configured to route a gas into the spaces between the nanotubes, and a gas outlet configured to route the gas away from the spaces between the nanotubes. The apparatus further includes a fluid inflow path configured to route incoming fluid to at least one of the units and a fluid outflow path configured to route outgoing fluid from at least one of the units.

In some embodiments, the units are interconnected so that the fluid flows through the units in series. In some embodiments, in each of the units, each of the nanotubes is perpendicular to the substrate, each of the channels is perpendicular to the substrate, each of the channels has a diameter between 2 and 500 µm, and the nanotubes have a diameter between 5 and 20 nm. In some embodiments, in each of the units, the nanotubes are disposed on the substrate in an array configuration, with a plurality of voids in the array, with each of the voids corresponding to a respective channel. In some embodiments, the units are interconnected so that the fluid flows through the units in series.

Another aspect of the invention is directed to a method for interacting a fluid with a gas. This method includes the step of providing a plurality of fluid flow channels that are surrounded by nanotubes, each of the channels having an inflow end and an outflow end, wherein each of the channels is wide enough for a fluid to flow through, and wherein the nanotubes are spaced close enough to each other to retain the fluid within the channels when the fluid is flowing through the channels. This method also includes the steps of passing fluid through the through the channels and passing a gas through the spaces between the nanotubes outside the fluid flow channels, wherein the gas interacts with the fluid in the channels.

In some embodiments, each of the channels has a diameter between 2 and 500 nm. In some embodiments, the nanotubes have a diameter between 5 and 20 nm. In some embodiments, the nanotubes are spaced on centers that are between 1.5 times the diameter of the nanotubes and 5 times the diameter of the nanotubes. In some embodiments, the interaction between the gas and the fluid in the channels comprises an exchange of gasses. In some embodiments, the interaction between the gas and the fluid in the channels comprises an exchange of heat.

DESCRIPTION OF THE PREFERRED EMBODIMENTS

The present invention relates to a Gas Exchanger ("GE") that will be described here within the framework of an artificial lung for efficient gas exchange ($O_2$, $CO_2$, etc.) between compartments such as human (or animal) blood and ambient air or some other gas. The main examples described herein are an artificial lung and respiratory aid based on a structure made of nanotubes.

Figure 2A:
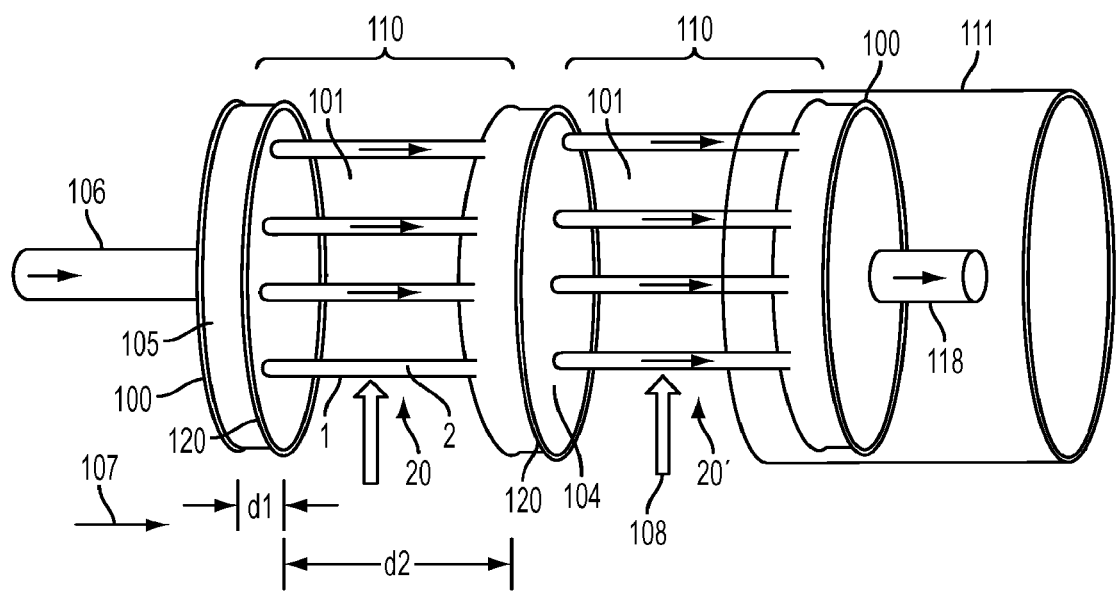
FIG. 2A is a schematic representation of a gas exchanger that has two gas exchange units of a first type connected in series.

The GE system contains one or more gas exchange units 110 (GEU), and FIG. 2A is a schematic representation of two such GEUs connected in series. Each GEU 110 includes a matrix of parallel aligned Blood Flow Channels 2 ("BFC"). FIG. 2A schematically depicts a first set 20 of four parallel BFCs in one GEU on the left, and a second set 20' of four parallel BFCs in a second GEU on the right, with the first GEU connected in series with the second GEU. Note that while FIG. 2A schematically depicts only four parallel BFCs in each GEU, in practice there will be many more BFCs in each GEU. For example, if the BFCs are 20 µm in diameter and are spaced on 40 µm centers, 62,500 BFCs would fit in a 1 cm² area. Note also that while FIG. 2A depicts two GEUs in series, that number may vary, and a given GE could have more than two GEUs in series, or only a single GEU. In alternative embodiments, a plurality of GEUs may be connected in parallel instead of in series.

Figure 3A:
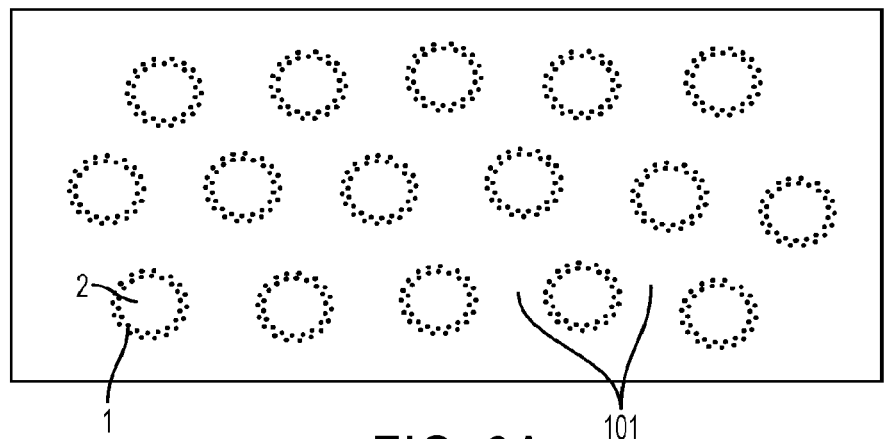
FIG. 3A depicts a preferred way to lay out the nanotubes for the FIG. 2B embodiment.
Figure 3B:
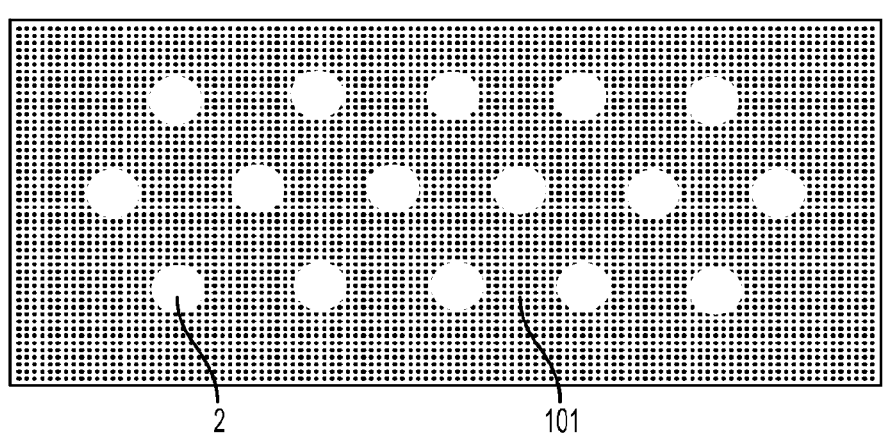
FIG. 3B depicts a preferred way to lay out the nanotubes for the FIG. 2A embodiment.

Each BFC is surrounded by Nanotubes, which are shown in FIG. 3B (but not shown in FIG. 2A). FIG. 3B depicts a preferred way to lay out the NTs to define the BFCs for the FIG. 2A embodiment, with the NTs laid out in a field pattern. The view depicted in FIG. 3B is a cross section through the BFCs and the NTs, and there are voids in the field of NTs that define the BFCs 2. In some embodiments, the diameter of the voids is between 2 and 500 µm, and in some embodiments the diameter is between 5 and 20 µm. (Note that all the figures in this application are not drawn to scale). The NTs within the field (i.e., outside the voids) are preferably arranged as a two dimensional matrix. The NTs preferably have diameters in the order of 1-100 nm, more preferably between 5 and 20 nm, and still more preferably between 10 and 20 nm. The optimum distance between the NT centers will be related to the NT diameter, so that the NTs do not end up too far away from each other. More specifically, when thinner NTs are used, the NTs should preferably be packed more closely together. Preferably, the spacing between NTs will be not more than a few diameters of the NTs, and will more preferably be on the order of 1 diameter. For example, if NTs with 10 nm diameter are used, the NTs would preferably be spaced on centers of about 20 nm, which would mean that the spacing between adjacent NTs would be around one diameter. But if NTs with 20 nm diameter are used, the NTs would preferably be spaced further apart, on centers of about 40 nm. A suitable relationship between the NT diameter and the NT spacing is to space the NTs on centers that are between 1.5 times the diameter of the NT and 5 times the diameter of the NT. For example, if NTs with a diameter of 10 nm are used, the NTs should preferably be spaced on centers between 15 and 50 nm. In less preferred embodiments, the NTs are spaced centers between 1 times and 10 times the diameter of the NTs, or even between 0.5 times and 20 times the diameter of the NTs. Note that the NT packing or density affects the resistance to flow of the gas through the "forest" of NTs, which is an additional consideration that may be adjusted depending on the specific need.

Figure 1A:
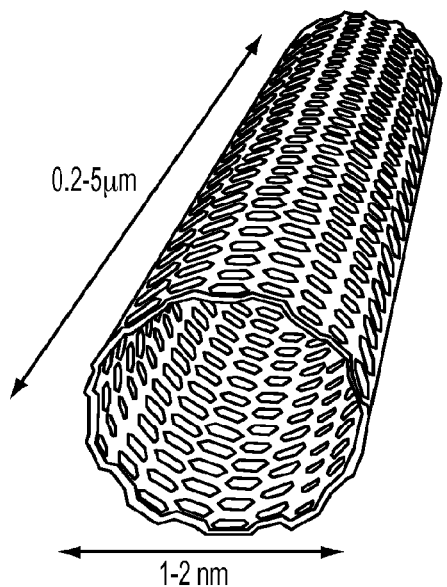
FIG. 1A depicts a single wall nanotube made of carbon.
Figure 1B:
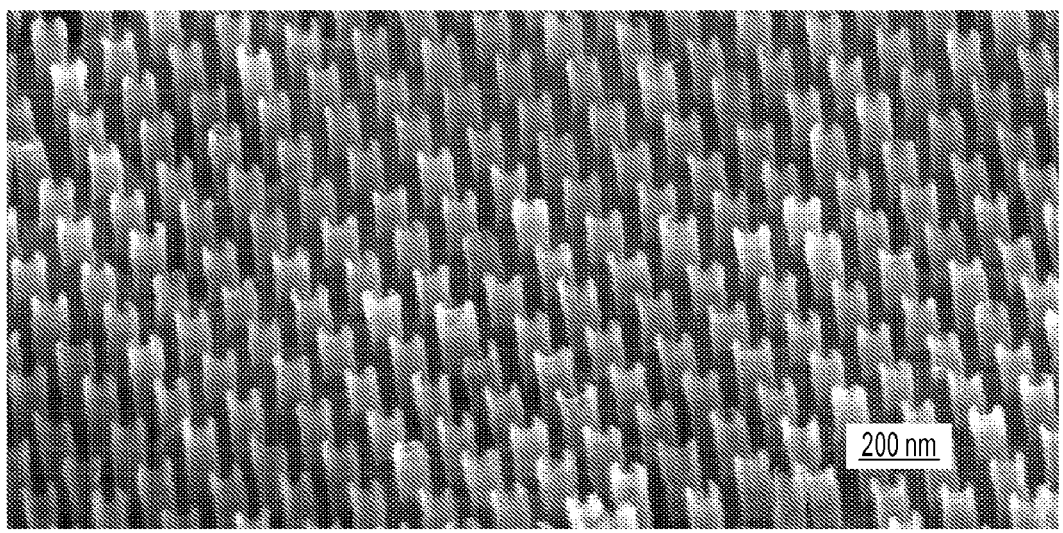
FIG. 1B is a scanning electron microscope photo of a matrix of parallel aligned carbon nanotubes.

Methods for fabricating large masses of parallel carbon NTs, as depicted in FIG. 1B, were described by Li et al. in Highly-Ordered Carbon Nanotube Arrays for Electronics Applications, Applied Physics Letters (1999); 75, 367-369. The desired placement of the NTs can be achieved by positioning the NTs at the desired locations using standard techniques. For example, the NTs may be fabricated on a substrate (which serves as a NT base) at the desired position using a lithography-based process. This may be accomplished by depositing catalysts on a substrate that has been masked to create the desired pattern, and then exposing it to carbon gas. The carbon from the gas then forms NTs (by self-assembly) on the spots where the catalyst has been deposited. NTs will not grow on the other parts of the substrate.

Returning to FIG. 2A, blood flows through the depicted device from left to right, in the blood flow direction 107. Blood that originates from the person's blood circulation flows through the Inflow channel 106 into an initial blood pool 105 that is bounded by a support 100 on the left, by the first NT base 120 on the right, and by casing 111 in directions that are perpendicular to the blood flow direction 107. In alternative embodiments, the boundary of the blood pool in directions that are perpendicular to the blood flow direction 107 can be implemented using an appropriate ring enclosure. The width of the initial blood pool is d1, and a suitable dimension for d1 is between 0.1-4 mm. However, any distance d1 that permits blood flow without adding a significant resistance to flow can be used instead.

The NT base 120 is preferably the substrate on which the NTs that surround the BFCs were fabricated, and the NT base 120 should have a hole or perforation 104 located at the center of each BFC. The NTs extend to the right from the NT base 120 and span a distance d2 to define the BFCs, which are oriented parallel to the direction of blood flow 107 and perpendicular to the gas flow direction 108. In some preferred embodiments, the distance d2 is between 0.1-1 cm. Because the NTs are grown on the NT base 120 and remain attached to it, no leakage near the base is expected. The NTs are held firmly in place by the extremely strong Wan der Vaals forces characterizing such nm scale structures. As a result of this configuration, blood that flows into the pool 105 will flow to the right through the perforations 104 in the NT base 120 and continue towards the right into and through the first set 20 of BFCs 2 in the first GEU.

A second NT base 120 is preferably positioned a short distance (e.g., between 0.1-4 mm in some embodiment or between 0.5 and 2 mm in some embodiments) away from the right end of the NTs that define the first set 20 of BFCs 2. When blood exits the first set of BFCs, it will flow into the gap between (a) the right end of the NTs that define the first set 20 of BFCs 2 and (b) the second NT base 120. The second GEU has a second set 20' of BFCs 2 that is similar in construction to the first set 20 of BFCs 2, each BFC having an aligned perforation 104 in the NT base. The blood that enters the gap will then flow to the right through the perforations 104 in the second NT base 120 and continue towards the right, into and through the second set 20' of BFCs 2 in the second GEU.

Note that when the blood exits the first set 20 of BFCs 2 and flows into the gap, surface tension of the blood (which is a water-based liquid) together with the hydrophobicity of the carbon NTs should prevent the blood from backing up into the very small spaces between the NTs that form the first set 20 of BFCs 2. Instead, the blood should flow to the right into the second set 20' of BFCs 2 in the second GEU, because the diameter of the BFCs in the second GEU is orders of magnitude larger than the very small spaces between the NTs in the first GEU. The blood would then flow according to the pressure gradient through the second GEU (i.e., in the blood flow direction 107 through the holes in the second NT base 120 and then through the second set 20' of BFCs 2 in the second GEU) rather than backwards. Note that the distance between adjacent NTs (i.e., less than a few diameters of the NTs, and preferably on the order of 1 diameter) is low enough to prevent blood plasma (or water) from penetrating the space between the NTs due to surface tension.

In alternative embodiments, additional stages (not shown) may be added in series. The blood eventually reaches the last GEU. A final support 100 is preferably positioned a short distance (e.g., between 0.1-4 mm in some embodiments, or between 0.5 and 2 mm in some embodiments) away from the right end of the NTs that define the last set 20' of BFCs 2. When blood exits the last set of BFCs, it will flow into the gap between (a) the right end of the NTs that define the last set 20' of BFCs 2 and (b) the final support 100. From there it will flow into the blood outflow channel 118.

While the blood is in the BFCs 2 in any of the stages, the blood has a chance to interact with the gases in the gas flow region 101. These gases flow in a gas flow direction 108 (i.e., up in FIG. 2A) that is preferably perpendicular to the direction of blood flow 107 (i.e., to the right in FIG. 2A). At the end of this process the blood continues through outflow channel 118, back to the blood circulation. It is important to note that the BFCs have no coating or membrane to keep the blood from escaping the BFC. However, due to the high density of the hydrophobic NTs surrounding the BFCs and the high surface tension of water, when a water-based fluid, such as blood, occupies or flows in the BFC, it will not leak out of the BFCs into the gas flow region 101. In other words, the NTs surrounding the BFC form a virtual boundary for the liquid flow.

Casing 111, a rigid biocompatible housing, seals the initial Blood Pool 105 as well as the one or more GEUs 110 contained within the casing 111. This permits gas exchange between the blood in the BFC and the air (or other gases) in the gas flow regions 101.

Figure 2B:
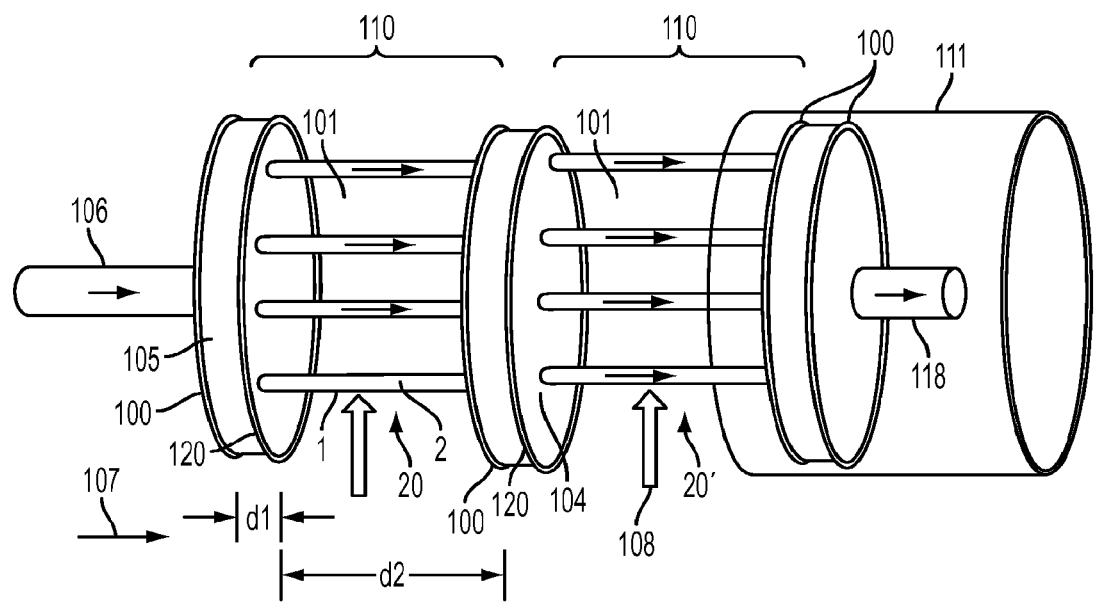
FIG. 2B is a schematic representation of a gas exchanger that has two gas exchange units of a second type connected in series.

FIG. 2B depicts an alternative embodiment that is similar to the FIG. 2A embodiment, except that additional blood pools 105 are added between adjacent GEU stages. In this embodiment, blood exiting one GEU is collected into a blood pool 105 confined between a planar support 100 (on the left) and the subsequent NT base 120 before it enters the next GEU. The planar support 100 for each GEU stage has holes or perforations 104 that are aligned to the position of the BFCs 2 of the previous stage GEU (except for the input of the first stage and the output of the last stage, which preferably each have a single larger port). For any given stage, the distance between the planar support 100 and the subsequent NT base 120 is d1, and a suitable dimension for d1 is between 0.1-4 mm. However, any separation that permits blood flow without adding a significant resistance to flow can be used instead. Casing 111, a rigid biocompatible housing, seals all the Blood Pools 105 as well as all the GEUs 110 contained within the casing 111.

In this FIG. 2B embodiment, the NTs may be laid out as shown in FIG. 3B, which is discussed above. But alternative layouts for the NTs may also be used in this embodiment.

FIG. 3A depicts a first alternative approach for laying out the NTs to define the BFCs in the FIG. 2B embodiment. In this approach, the NTs are laid out in pattern of rings 1 so that the inner boundary of each ring 1 defines a BFC 2. The depicted view is a cross section through the BFCs and the NTs. The diameter of the inner boundary of the ring is between 2 and 500 μm in some embodiments, and between 5 and 20 μm in some embodiments. In this approach, the thickness of each ring (i.e., the distance between the innermost NTs of the ring and the outermost NTs of the ring) is preferably between 100 nm and 10 μm, and the NTs within the ring are preferably spaced on centers between 10 and 100 nm. As in the FIG. 3B approach, the distance between the NT centers is preferably related to the NT diameter, so that the NTs do not end up too far away from each other. FIG. 3D is a detailed view of a ring 1 and the BFC 2 of FIG. 3A. The NTs in the ring 1 may be laid out in a two dimensional matrix, as shown in FIG. 3D, or in any other layout that maintains appropriate spacing between the centers of the NTs.

Figure 3C:
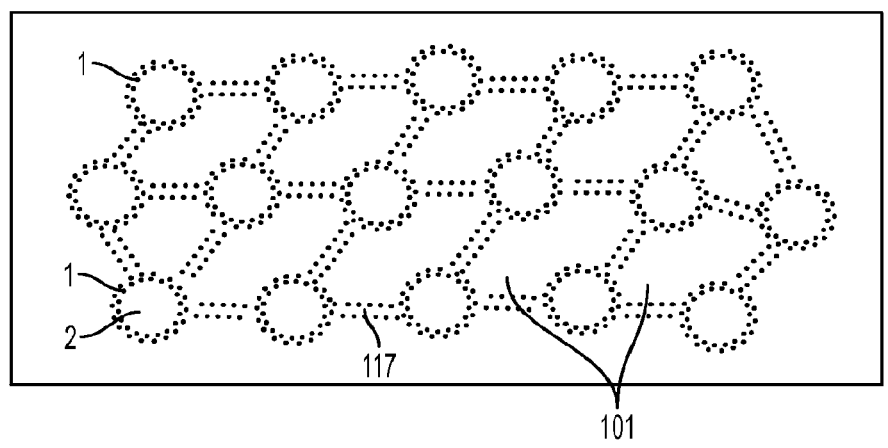
FIG. 3C depicts another preferred way to lay out the nanotubes for the FIG. 2B embodiment.
Figure 3D:
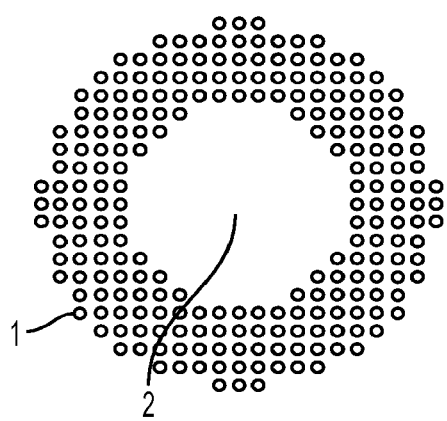
FIG. 3D is a detailed view of FIG. 3A.

FIG. 3C depicts a second alternative approach to lay out the NTs to define the BFCs in the FIG. 2B embodiment. The depicted view is a cross section through the BFCs and the NTs. This approach is similar to the approach depicted in FIG. 3A, except that additional NTs are added to provide structural support. The additional NTs may be configured to form support bridges 117, as shown in FIG. 3C, but alternative layouts for the additional NTs may be used instead. Examples of such alternative layouts (not shown) include stripes and grids. The layout of the additional NTs may be selected to provide structural strength without unduly increasing the resistance to air flow. Another example (not shown) would be to add clusters of NTs at midpoints between adjacent BFCs, arranged in a column-like fashion to add structural support. For example, a set of NTs arranged to fill in a circle with a diameter of 10 μm, with the NTs in the set spaced on centers between 10 and 100 nm, could serves as a support column. Each NT in such a support column would have the same length d2 as the NTs in the rings that surround the BFCs.

For all of the embodiments described above, the blood in the inflow channel 106 is preferably venous blood that is low in oxygen and rich in $CO_2$. The two blood gases undergo an exchange with the gas flowing in the gas flow region 101 around the BFCs in a direction 108 that is preferably normal to that of the BFC blood flow 107. This incoming gas is preferably rich in oxygen and has a low or zero concentration of $CO_2$ so that the gas exchange is by diffusion along the concentration gradients. The blood in the outflow channel 118 will then be richer in $O_2$ than the incoming blood.

The efficacy of the gas exchange is a function of the area of contact between the flowing blood and the flowing gas that may be oxygen or air. As mentioned above, in a normal pair of lungs this contact surface area is typically about 70 $m^2$ while the blood flow is 5-7 L/min and air flow is similar. The amount of Oxygen or $CO_2$ exchanged in normal human lungs is typically 200-250 $cm^3$/min.

Let us now compute the parameters of gas exchange that satisfy the normal physiological requirements: The total BFC surface area that is needed for the gas exchange is a direct function of the BFC diameter and packing, i.e. the distance between the BFCs, and the total number of BFCs in the GE volume. For a GE having a total volume of 2 liters (e.g., 10 cm×10 cm×20 cm), the surface area available for exchange is independent of the arrangement of the GEUs within the GE, i.e. in series or in parallel, or their spatial configuration. For such a GE, if we assume that the BFC Radius is 10 μm, and the center-to-center distance of the BFCs is 40 μm, the total gas-blood exchange area is close about 80 $m^2$, which is approximately equal to a typical pair of lungs. The Diffusion Capacity will therefore be over 2000 $cm^3$ $O_2$ per min (which exceeds the requirement of 250 $cm^3$/min), and the Blood volume will be about 400 $cm^3$ (which is comparable to that of the adult human respiratory system).

Figure 4A:
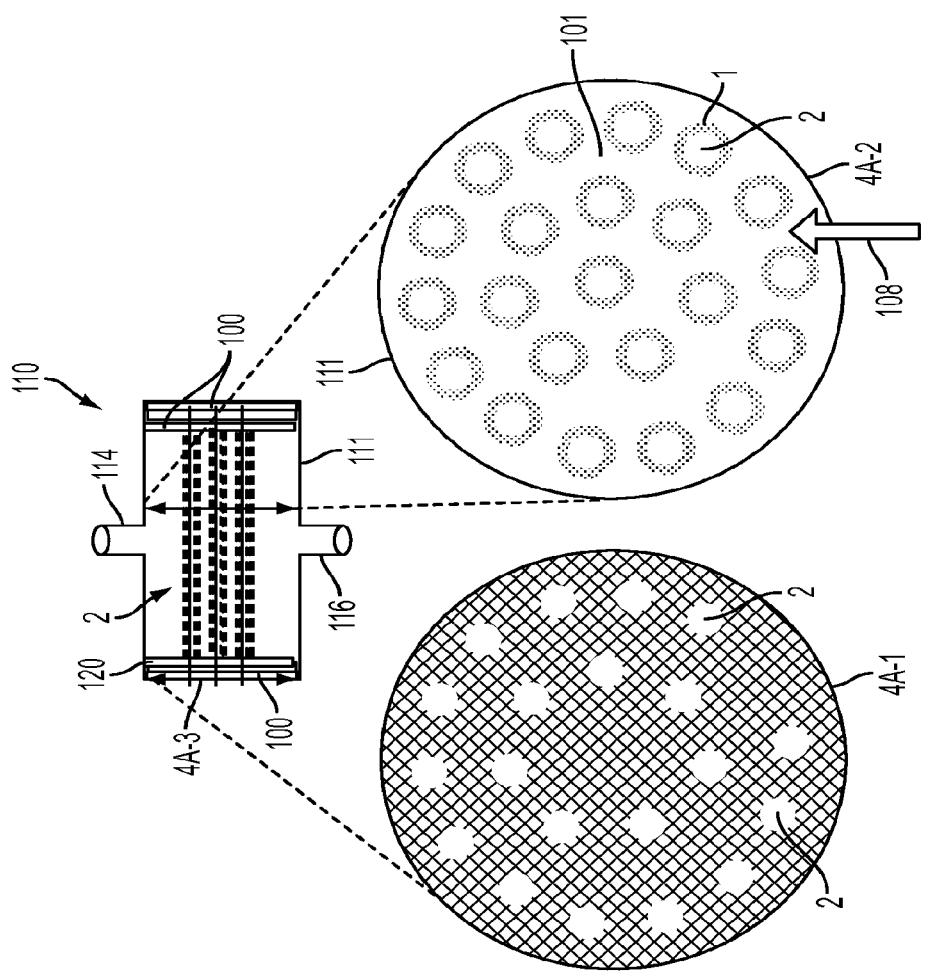
FIG. 4A is a more detailed representation of a single gas exchange unit of the FIG. 2B embodiment.
Figure 4B:
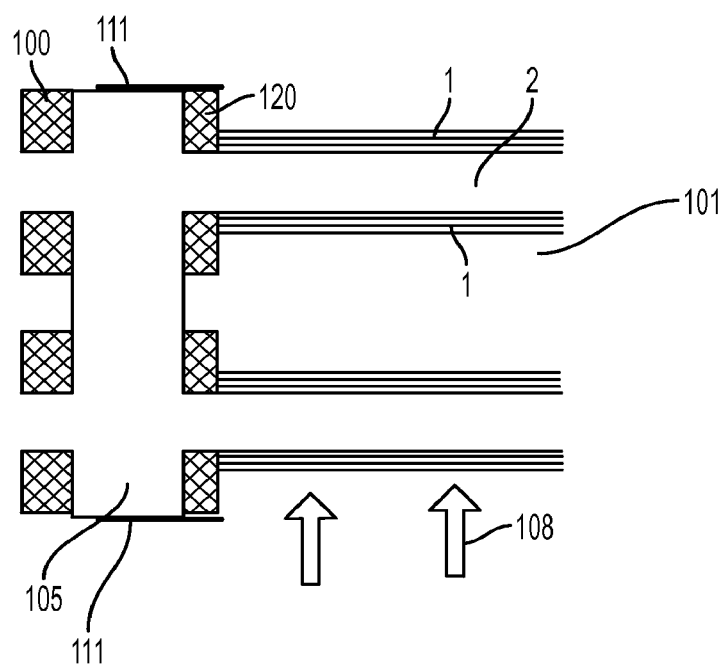
FIG. 4B is a magnified view of a region of FIG. 4A.

FIG. 4A is a more detailed representation of a single GEU 110 of the FIG. 2B variety, in which the NTs are arranged in rings 1 (as shown in FIGS. 3A and 3D). The GEU 110 has a set of parallel BFCs located between a first support 100 and a first NT base 120 on the left and a pair of supports 100 on the right. The $O_2$ rich gas flows into the gas inlet 116, flows past the BFCs 2, and exits the gas outlet 114. As the gas flows past the BFCs 2, it comes in contact with the blood in the BFCs so that gases can be exchanged. 4A-1 is a cross section through the first support 100, which shows the holes in the support, and 4A-2 is a cross section through a set of BFCs 2. The holes in the NT base 120 line up with the BFCs, as best seen in FIG. 4B, which is a magnified view of the region 4A-3 of FIG. 4A. The holes in the support 100 also line up with the BFCs of the previous stage, as best seen in FIG. 4B. Note that although FIG. 4A schematically shows only 22 BFCs, there will in fact be many more BFCs that are spaced much more closely together, as described above.

The overall GE preferably includes a plurality of GEUs connected together. The GEUs may be connected in series or in parallel to form the GE. Since connecting GEUs in series will increase the flow resistance, the number of GEUs that are connected in series should preferably be limited (e.g., to not more than ten). The GEUs may also be connected in a series/parallel combination. For example, three GEUs may be connected in series, and then the resulting set of three GEUs may be connected in parallel with five similar sets of three series-connected GEUs. Different series/parallel combinations may also be used.

The number of GEUs that are used in any given GE may vary, depending on the required surface area for diffusion. In some embodiments, a GE may contain between 2 and 20 GEUs connected in series, or between 2 and 10 GEUs connected in series.

Figure 5:
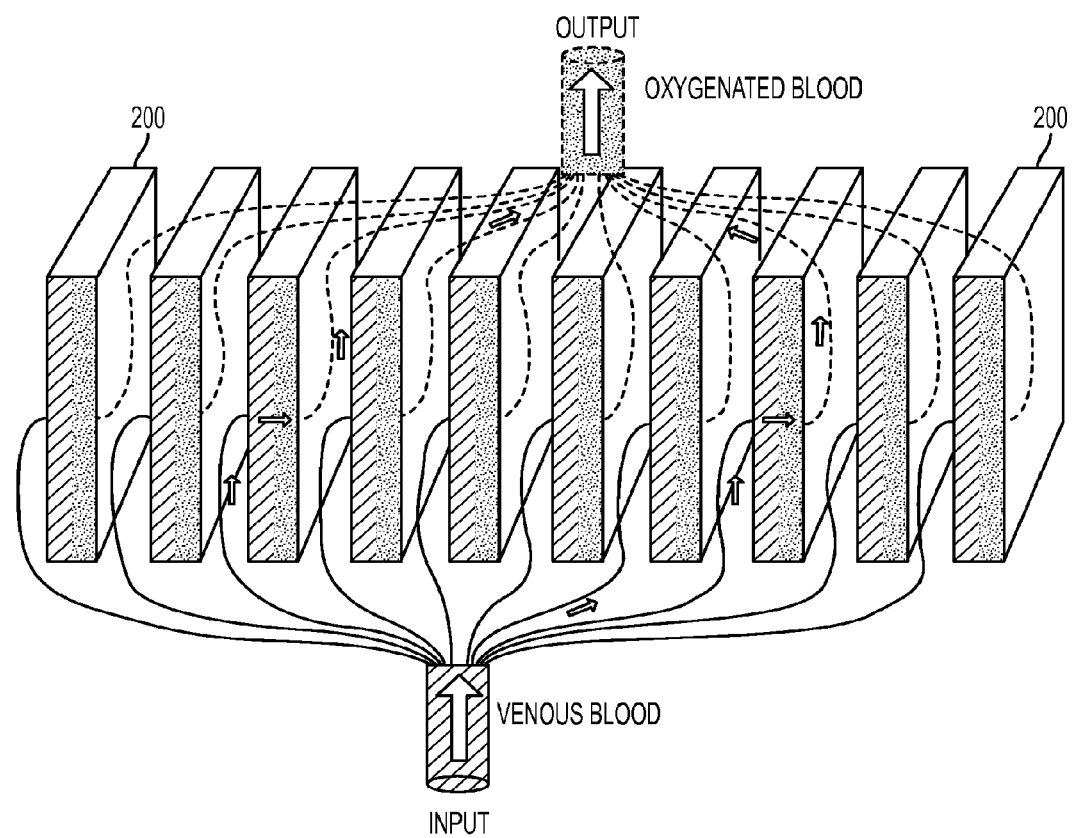
FIG. 5 depicts a gas exchanger with ten gas exchange units connected in parallel.

Optionally, a plurality of GEUs may be combined into subsystems, and those subsystems may be connected in series, in parallel, or in series/parallel combinations to form the overall GE. When the BFCs are 20 μm in diameter and are spaced on 40 μm centers, 62,500 BFCs would fit in a 1 $cm^2$ area, and would impose resistance to flow through the BFCs of $1.63 \cdot 10^5$ g/(s $cm^4$). One example of suitable dimensions for a subsystem for use in a GE would be a width of 10 cm, a height of 10 cm, and a thickness of about 1.1 cm. The 1.1 cm thickness could be made of 10 GEUs that are each 0.1 cm thick, arranged in series as depicted in FIG. 2A, separated by 9 NT bases 120 that are each 0.1 mm thick between the GEUs, plus an additional blood pool 105 at each end. These 10×10×1.1 cm subsystems can then be configured in parallel to make the complete GE. FIG. 5 depicts ten such subsystems 200 connected in parallel. When 20 such subsystems are arranged in parallel, resistance to flow will be sufficiently low so that less than 50 mmHg is required to induce the required 5-7 L/min blood flow (for subsystems of 10 cm×10 cm×1.1 cm each with the BFC diameter and spacing described above). The Dwell Time (i.e., the time flowing blood is exposed to gas exchange when flowing from input to output) for this configuration will be over 1 sec, which is well above the required minimal value of 0.2-0.4 sec.

In alternative configurations, the subsystems may be smaller e.g., 2 cm wide, 2 cm high, and about 1 cm thick, with similar internal construction to the 20×20×1.1 cm subsystems described above. These 2×2×1 cm subsystems can then be configured in parallel and/or in series to form the complete GE. In other alternative embodiments, the subsystems may be larger (e.g., 20 cm wide, 20 cm high, and about 2 cm thick).

Yet another possible configuration of GEUs for forming a GE would be to connect 2000 1 $cm^2$ units in parallel into a subsystem, and then connect 10 such subsystems in series. In such a GE system, the surface area of oxygen diffusion is sufficient for physiological quiet breathing and the resistance to flow in the BFCs would be only 815 g/(s $cm^4$). This configuration would also have a pressure drop of less than 50 mmHg when 5-7 L/min of blood is flowing through the system.

Note that the diffusion capacity of the GEs discussed herein can be even higher than human lungs in which a 0.5-1 μm membrane (made up of living cells and a basal membrane) is interposed between the air and blood. In contrast, there is a direct air-blood contact in the GE. The continuous gas flow around the BFCs in the GE is also more efficient than the in/out air flow in the lungs during natural respiration.

We turn next to the efficacy of the Gas Exchanger with regards to $CO_2$. The water Diffusion coefficients of $CO_2$ and $O_2$ are similar while the solubility of $CO_2$ is about 24 times higher than that of O2. As the $O_2$ and $CO_2$ concentration difference between oxygenated and reduced blood are similar, the diffusion rate of $CO_2$ is about 20 times that of $O_2$.

Thus, the $CO_2$ transport in all the above processes is expected to be superior to that of $O_2$.

Two examples of clinical applications are using the GE as an artificial lung and using the GE as a respiratory assist device.

Figure 6A:
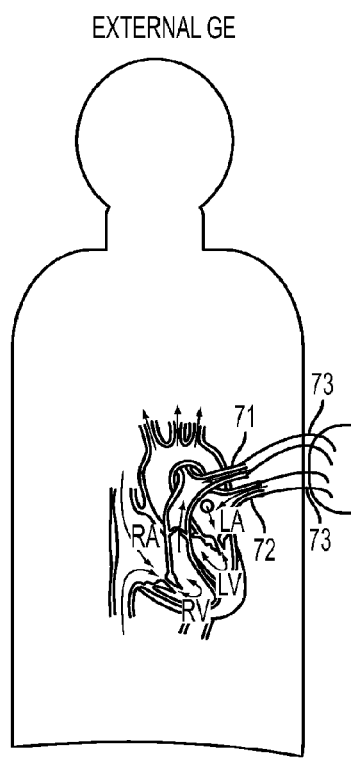
FIGS. 6A, 6B, and 6C depict three ways how a gas exchanger can be used as an artificial lung.
Figure 6B:
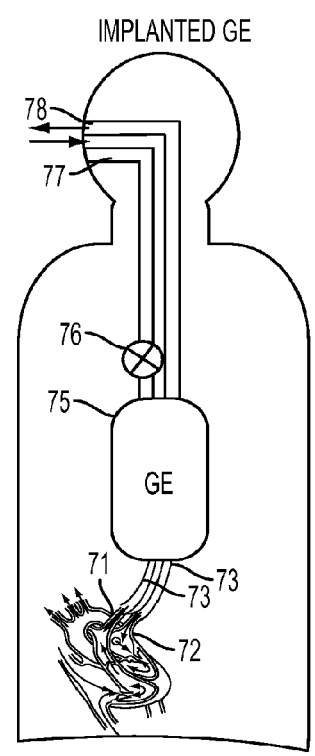
Figure 6C:
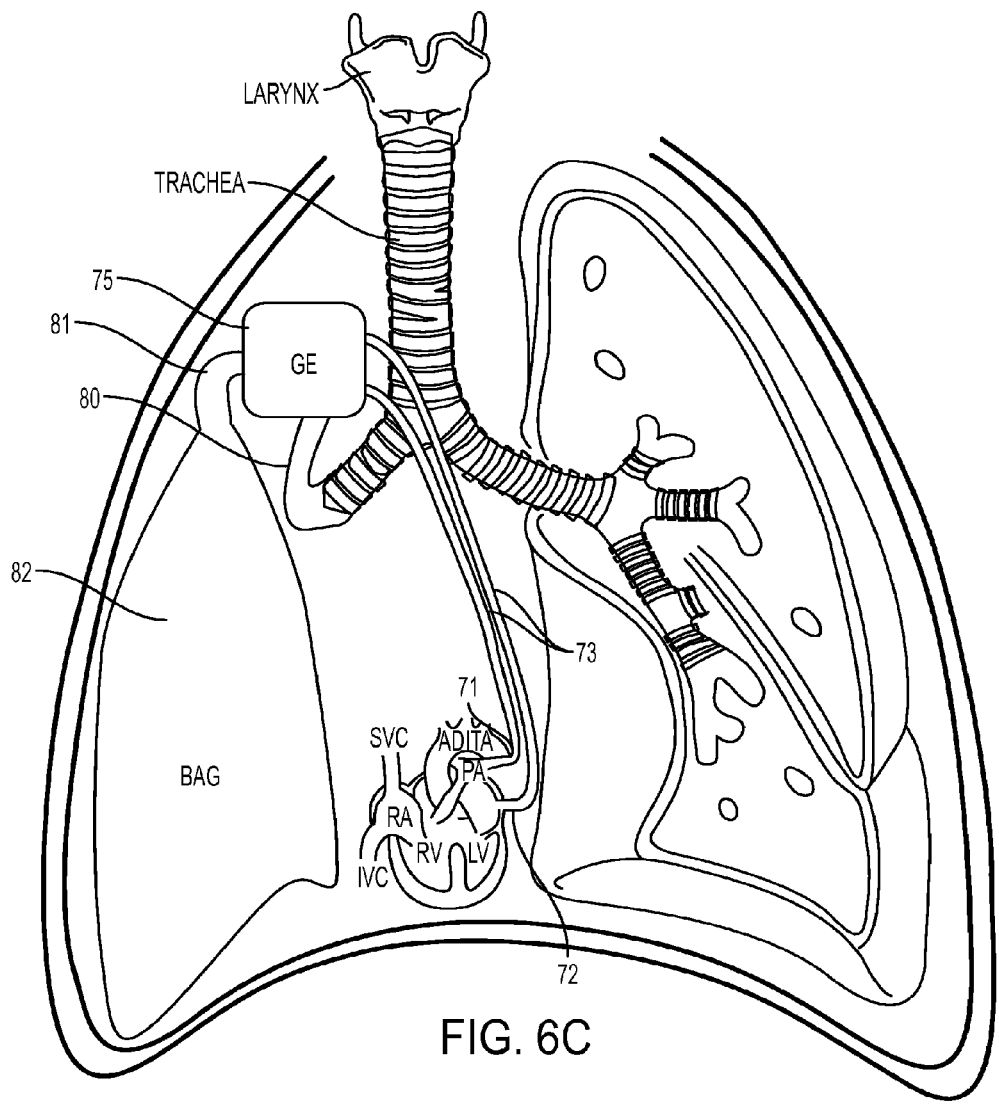

FIGS. 6A, 6B, and 6C depict how a GE 75 can be used as an artificial lung, in which case the GE 75 replaces either one or both lungs. In this application, the GE may be implanted (as shown in FIGS. 6B and 6C) or external (as shown in FIG. 6A). In either case, the blood enters the GE 75 via tubing 73 from the pulmonary artery 71 and the blood is returned to the pulmonary vein 72 from the GE via tubing 73. Air or oxygen can be pumped into the GE 75 via the gas input tube 77 by pump 76 and the exhaust leaves via the exhaust tube 78, as shown in FIGS. 6A and 6B.

Alternatively, air can be driven through the trachea and main bronchi via natural breathing as shown in FIG. 6C. In this case the air flows in tube 80 from the bronchi into the GE 75 that is connected via tube 81 to an expandable gas bag 82, which inflates and deflates, i.e. changes volume during inspiration and expiration, respectively. Tubes 80 and 81 serve also as the exhaust tubes for the gas exiting the bag 82 via the GE 75 back into the main bronchi and environment.

In any of these embodiments, the blood flow can be maintained by the natural pressure generated by the right ventricle or an appropriate blood vessel. Alternatively it can be driven by an external or implanted pump designed to generate blood flow for long periods of time. Such pumps are commercially available. The blood exiting the GE is returned to the body via a pulmonary vein 72 or veins, or any other appropriate blood vessel.

The flow rates for both blood and air are preferably adjustable to match the needs of the person, etc. this adjustment may be dynamic according to the changing need, for example during exercise. The adjustment may be controlled by sensors of a relevant physiological parameter such as the partial pressure of $O_2$ and/or $CO_2$ in the blood, Hb $O_2$ saturation (oximetry), pH, etc. To supply the $O_2$ (or other gas) needs, which amount to approximately 250 $cm^3$/min for a resting adult man, a flow of about 5-7 L/min oxygenated blood is required; and this may need to be increased by a factor of up to 4-5 during exercise. An additional factor that should preferably be taken into consideration is the time the flowing blood is exposed to the gas diffusion process, the dwell time. In the normal resting human lung this duration is about ⅓-⅕ of a sec while the flow velocity is usually under 100 cm/s. The blood flow in the GE is compatible with these requirements. When the subject's heart is healthy, the blood flow may be powered by the patient's heart. Note that the series/parallel configuration of GEUs within the GE may be selected in advance to provide a desired flow resistance. To increase the resistance, the number of GEUs connected in series should be increased. To decrease the resistance, the number of GEUs connected in series should be reduced, and the number of parallel connections should be increased.

The corresponding air (or oxygen) flow is also about 5-8 L/min at rest and up to 5 times larger during exercise. When implanted, the Gas inlet 116 and Gas Outlet 114 (shown in FIG. 4) can be connected to the patient's bronchial system as shown in FIG. 6C and flow can be maintained by respiratory movements or a by an appropriate pump. When the GE is external (as shown in FIG. 6A) or implanted without the use of the respiratory ventilation ability (FIG. 6B), the gas Inlet & Outlet are preferably in communication with the ambient air or a gas reservoir through appropriate filters. In this case, gas flow can be continuously driven by an appropriate pump and regulated by appropriate sensors.

Figure 7:
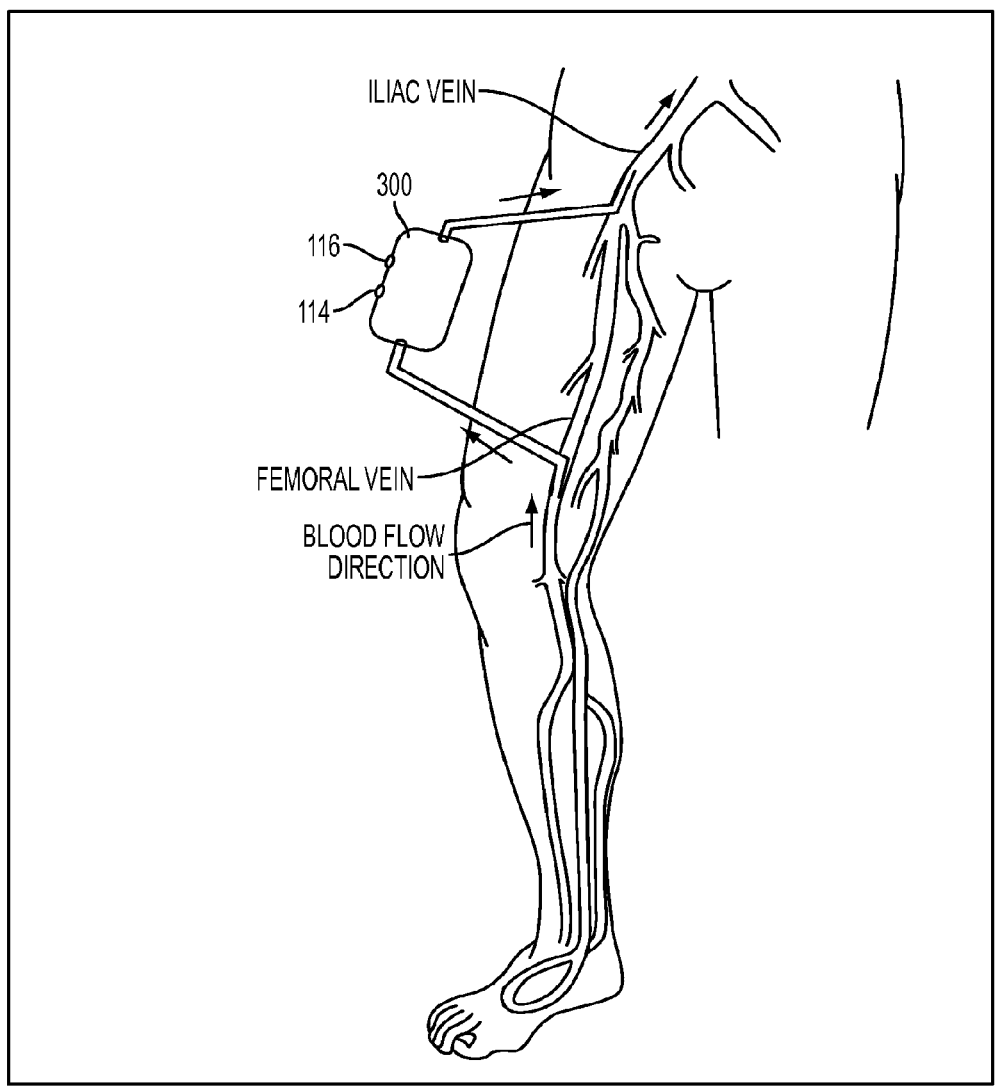
FIG. 7 is a schematic representation of how a gas exchanger can be used as a respiratory assist device.

FIG. 7 is a schematic representation of how the GE can be used as a respiratory assist device, in order to provide additional oxygenation of blood for a patient with a failing respiratory system. In these cases the GE 300 is positioned externally, as shown, or implanted. In this application, the blood flowing through the GE is preferably derived here from a large blood vessel, for example the femoral vein. The blood exiting the GE can be introduced back into the femoral vein or veins, or any other appropriate blood vessel.

Note that the embodiments described above are described using nanotubes. In alternative embodiments, the nanotubes described above may be replaced with other species of hydrophobic pillar-shaped structures with diameters between 1 and 100 nm. For example, in some embodiments, hydrophobic nanofibers, nanorods, or nanowires with diameters between 1 and 100 nm may be used in place of the nanotubes described above.

The invention is described above in the context of delivering $O_2$ to blood and removing $CO_2$ from blood. But the invention is not limited to that application, and can be used to deliver other gases to blood. For example, it may be used in connection with a body part that has a dedicated circulation (such as a leg, brain, kidney) to deliver any desired gas to that body part. This can be used to deliver a chemical such as an anesthetic or therapeutic gas intended to act locally. In such a case the gas will be inputted into the artery and outputted (eliminated) via the vein, etc.

Note that in other types of GEs, fluids other than blood may be utilized. The invention is also not limited to medical uses, and can be used to exchange gases in other types of fluid flow systems, including industrial applications.

As additional use of the apparatuses described above is as a heat exchanger. Regardless of whether any gases are exchanged between the gas and liquid that flow through the device, heat transfer can still occur between the gas and the fluid. As a result, hot fluid can be used to heat the gas, cold fluid can be used to cool the gas, hot gas can be used to heat the fluid, or cold gas can be used to cool the fluid. The heat transfer is expected to be very effective relative to prior art devices because the contact surface area is very large, and there is no physical barrier between the gas and the fluid. Optionally, sensors and pumps may be used to control the exchange so as to maintain the desired temperature. These sensors and pumps may also be used when the primary purpose is gas exchange, as in the embodiments described above.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

I claim:

1. A gas exchanger apparatus comprising:
    a substrate having a first side and a second side;
    a plurality of hydrophobic pillar-shaped structures with diameters between 1 and 100 nm disposed on the second side of the substrate with spaces between the pillar-shaped structures, wherein the pillar-shaped structures are disposed on the substrate in a configuration that leaves a plurality of fluid flow channels that are surrounded by the pillar-shaped structures, each of the channels having an inflow end and an outflow end, wherein each of the channels is wide enough for a fluid to flow through, and wherein the pillar-shaped structures are spaced close enough to each other to retain the fluid within the channels when the fluid is flowing through the channels, and wherein the substrate has a plurality of perforations that extend between the first side of the substrate and the second side of the substrate, each of the perforations being aligned with a respective one of the channels;

a fluid inlet configured to supply fluid to the first side of the substrate, wherein the fluid inlet is in fluid communication with the perforations such that fluid that arrives via the fluid inlet will flow through the perforations and continue on through the channels;

a fluid outlet configured to accept fluid that arrives from the outflow end of the channels; and a housing configured to house the substrate and the array of pillar-shaped structures, the housing having a gas inlet configured to route a gas into the spaces between the pillar-shaped structures and a gas outlet configured to route the gas away from the spaces between the pillar-shaped structures.

2. The gas exchanger apparatus of claim 1, wherein each of the pillar-shaped structures is perpendicular to the substrate and wherein each of the channels is perpendicular to the substrate.

3. The gas exchanger apparatus of claim 1, wherein the pillar-shaped structures are disposed on the substrate in an array configuration, with a plurality of voids in the array, wherein each of the voids corresponds to a respective channel.

4. The gas exchanger apparatus of claim 1, wherein each of the channels has a diameter between 2 and 500 μm.

5. The gas exchanger apparatus of claim 1, wherein the pillar-shaped structures have a diameter between 5 and 20 nm.

6. The gas exchanger apparatus of claim 1, wherein the pillar-shaped structures are spaced on centers that are between 1.5 times the diameter of the pillar-shaped structures and 5 times the diameter of the pillar-shaped structures.

7. The gas exchanger apparatus of claim 1, wherein each of the pillar-shaped structures is perpendicular to the substrate, each of the channels is perpendicular to the substrate, each of the channels has a diameter between 2 and 500 μm, and the pillar-shaped structures have a diameter between 5 and 20 nm.

8. The gas exchanger apparatus of claim 7, wherein the pillar-shaped structures are spaced on centers that are between 1.5 times the diameter of the pillar-shaped structures and 5 times the diameter of the pillar-shaped structures.

9. The gas exchanger apparatus of claim 8, wherein the pillar-shaped structures are disposed on the substrate in an array configuration, with a plurality of voids in the array, wherein each of the voids corresponds to a respective channel.

10. The gas exchanger apparatus of claim 1, wherein the pillar-shaped structures are nanotubes.

11. The gas exchanger apparatus of claim 1, wherein the pillar-shaped structures are nanorods.

12. A gas exchanger apparatus comprising:

a plurality of units, each of the units including (a) a substrate having a first side and a second side, (b) a plurality of hydrophobic pillar-shaped structures with diameters between 1 and 100 nm disposed on the second side of the substrate with spaces between the pillar-shaped structures, wherein the pillar-shaped structures are disposed on the substrate in a configuration that leaves a plurality of fluid flow channels that are surrounded by the pillar-shaped structures, each of the channels having an inflow end and an outflow end, wherein each of the channels is wide enough for a fluid to flow through, and wherein the pillar-shaped structures are spaced close enough to each other to retain the fluid within the channels when the fluid is flowing through the channels, and wherein the substrate has a plurality of perforations that extend between the first side of the substrate and the second side of the substrate, each of the perforations being aligned with a respective one of the channels, (c) a fluid inlet configured to supply fluid to the first side of the substrate, wherein the fluid inlet is in fluid communication with the perforations such that fluid that arrives via the fluid inlet will flow through the perforations and continue on through the channels, and (d) a fluid outlet configured to accept fluid that arrives from the outflow end of the channels;

a housing configured to house the plurality of units, the housing having a gas inlet configured to route a gas into the spaces between the pillar-shaped structures, and a gas outlet configured to route the gas away from the spaces between the pillar-shaped structures;

a fluid inflow path configured to route incoming fluid to at least one of the units; and a fluid outflow path configured to route outgoing fluid from at least one of the units.

13. The gas exchanger apparatus of claim 12, wherein the units are interconnected so that the fluid flows through the units in series.

14. The gas exchanger apparatus of claim 12 wherein, in each of the units, each of the pillar-shaped structures is perpendicular to the substrate, each of the channels is perpendicular to the substrate, each of the channels has a diameter between 2 and 500 μm, and the pillar-shaped structures have a diameter between 5 and 20 nm.

15. The gas exchanger apparatus of claim 12 wherein, in each of the units, the pillar-shaped structures are disposed on the substrate in an array configuration, with a plurality of voids in the array, with each of the voids corresponding to a respective channel.

16. A method for interacting a fluid with a gas, the method comprising the steps of:

providing a plurality of fluid flow channels that are surrounded by hydrophobic pillar-shaped structures with diameters between 1 and 100 nm, each of the channels having an inflow end and an outflow end, wherein each of the channels is wide enough for a fluid to flow through, and wherein the pillar-shaped structures are spaced close enough to each other to retain the fluid within the channels when the fluid is flowing through the channels;

passing fluid through the through the channels; and passing a gas through the spaces between the pillar-shaped structures outside the fluid flow channels, wherein the gas interacts with the fluid in the channels.

17. The method of claim 16, wherein each of the channels has a diameter between 2 and 500 μm.

18. The method of claim 16, wherein the pillar-shaped structures have a diameter between 5 and 20 nm.

19. The method of claim 16, wherein the pillar-shaped structures are spaced on centers that are between 1.5 times the diameter of the pillar-shaped structures and 5 times the diameter of the pillar-shaped structures.

20. The method of claim 16, wherein the interaction between the gas and the fluid in the channels comprises an exchange of gasses.

21. The method of claim 16, wherein the interaction between the gas and the fluid in the channels comprises an exchange of heat.

\* \* \* \* \*